United States Patent
Curran et al.

(10) Patent No.: US 6,861,544 B1
(45) Date of Patent: Mar. 1, 2005

(54) FLUOROUS TIN COMPOUNDS AN METHODS OF USING FLUOROUS TIN COMPOUNDS

(75) Inventors: Dennis P. Curran, Pittsburgh, PA (US); Zhiyong Luo, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/602,105

(22) Filed: Jun. 22, 2000

(51) Int. Cl.$^7$ .................................................. C07F 7/22
(52) U.S. Cl. ............................. 556/88; 556/87; 556/95
(58) Field of Search .............................. 556/87, 88, 95

(56) References Cited

U.S. PATENT DOCUMENTS

| | | | | |
|---|---|---|---|---|
| 3,590,060 | A | * 6/1971 | Murch | 260/429.7 |
| 4,454,233 | A | 6/1984 | Wang | 436/525 |
| 5,401,847 | A | 3/1995 | Glazer et al. | 546/107 |
| 5,463,082 | A | 10/1995 | Horvath et al. | 549/46 |
| 5,777,121 | A | 7/1998 | Curran et al. | 546/2 |
| 5,798,032 | A | 8/1998 | Khan et al. | 204/452 |
| 5,859,247 | A | 1/1999 | Curran et al. | 546/2 |
| 6,156,896 | A | 12/2000 | Curran et al. | 546/2 |

FOREIGN PATENT DOCUMENTS

WO   WO/01/98312   12/2001

OTHER PUBLICATIONS

Curran et al., Bioorganic & Medicinal Chemistry Letters, vol. 8, No. 17, pp. 2403–2408 (1998).*

Bucher et al., Tetrahedron Letters, vol. 41, pp. 9617–9621 (2000).*

Curran et al., J. Am. Chem. Soc., vol. 121, pp. 6607–6615 (1999).*

Curran, D.P.: Hadida, S.; Kim. S. Y. Tris(2–perfluorohexylathyl) tin azide: A new reagent for preparation of 5–substituted tetrazoles from nitriles with pufication by fluorous organic liquid–liquid extraction. Tetrahedron 1999, 55, 8997–9006.

Curran, D.P.: Hadida, S.; Kim, S. Y.; Luo, Z. Y. Fluorous tin hydrides: A new family of reagents for use nad reuse in radical reactions. J. Am. Chem. Soc. 1999, 121, 6607–6615.

Curran, D. P.; Luo, Z.; Degenkolb, P. "propylene spaced" allyl tin reagents: A new class of fluorous tin reagents for allytations under radical and metal–catalyzed conditions. Biorrg. Med. Chem. Lett. 1998, 8, 2403–2408.

Ryu, I.; Ngiuma, T.. Minakata, S.; Komatsu, M.; Hadida, S. eta l. Hydroxymethylation of organic halides. Evaluation of a catalytic system involving a fluorous tin hydride reagent for radical carbonylation. Tetrahedron Lett. 1997, 38, 7883–7885.

Haney B.P. et al. Round trip radical reactions from acyclic Precursors to tricycle 5.3.1.02, Sundecanes. A new cascade radical cyclization appraoch to (plus or minurs)–isogymnor- nitrene and (plus or minus) –gymmomltrene. Journal of Organic CHemistry, American Chemistry SOciety. Easton, US, vol. 65, No. 7, 2000, pp. 2007–2013.

Bucher, B. et al. Selective sulfonylation of 1,2–diols and derivatives ctalyzed byt a recoverable fluorous tin oxide. Tetrahedron Lett., vol. 41, No. 49, 2000, pp. 9617–9621.

Kainz, S.; Luo, Z. Y.; Curran, D. P.; Leitner, W. Synthesis of perfluoroalkyl–substituted aryl bromides and their purifica- tion over fluorous reverse phase silica. Synthesis 1998, 1425–1427.

Larhed, M.; Hoshino, M.; Hadida, S.; Curran, D. P.; Hall- berg, A. Rapid fluorous stille coupling reactions conducted under microwave irradiation. J. Org. Chem. 1997, 62, 5583–5587.

Olofsson, K.; Kim, S. Y.; Larhed, M.; Curran, D. P.; Hall- berg, A. High–speed, highly fluorous organic reactions. J. Org. Chem. 1999, 64, 4539–4541.

Ryu, I.; Niguma, T.; Minakata, S.; Komatsu, M.; Luo, Z. Y. et al. Radical carbonylations with fluorous allyltin reagents. Tetrahedron Lett. 1999, 40, 2367–2370.

Curran, D. P. Combinatorial Organic Synthesis and Phase Separation: Back to the Future. Chemtracts–Org. Chem. 1996, 9, 75–87.

(List continued on next page.)

Primary Examiner—Porfirio Nazario-Gonzalez
(74) Attorney, Agent, or Firm—Bartony & Hare, LLP

(57) ABSTRACT

A method of carrying out a reaction comprising the steps of: mixing at least one organic reaction component with at least one fluorous reaction component having the formula:

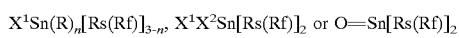

wherein n is 1 or 2, R is a $C_1$–$C_6$ alkyl group, $X^1$ and $X^2$ are independently, the same or different, H, F, Cl, Br, I, $N_3$, $OR^1$, $OOR^1$ $SR^1$, $SeR^1$, CN, NC, $NR^1R^2$, an aryl group, a het- eroaryl group, an alkyl group of 1 to 20 carbons, an alkenyl group, an alkynyl group, —C(O)$R^3$, M((Rs')(Rf'))$_3$, OM((Rs')(Rf'))$_3$ or OOM((Rs')Rf'))$_3$, wherein M is Si, Ge, or Sn, and wherein $R^1$ and $R^2$ are each independently the same or different H, an alkyl group, —SO$_2$$R^3$ or —C(O)$R^3$, wherein $R^3$ is an alkyl group or an aryl group, and wherein Rs and Rs' are each independently the same or different a spacer group, and wherein Rf and Rf' are each independently the same or different a fluorous group; carrying out a reaction to produce an organic product; and after producing the organic product, separating any excess of the fluorous reaction component and any fluorous byproduct of the fluorous reaction component using a fluorous separation technique. Several compounds have the formula:

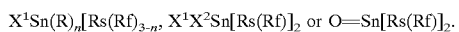

20 Claims, 5 Drawing Sheets

OTHER PUBLICATIONS

Curran, D. P. Strategy–level Separations in Organic Synthesis: From planning to practice. Angew. Chem. Int. Ed. Eng. 1998, 37, 1175–1196.

Curran, D. P. Parallel Synthesis with Fluorous Reagents and Reactants. Med. Res. Rev. 1999, 19, 432–438.

Curran, D. P; Hadida, S. Tris(2–(perfluorohexyl)ethyl)tin hydride: A new Fluorous Reagent for Use in Traditional Organic Synthesis and Liquid Phase Combinatorial Synthesis. J. Am. Chem. Soc. 1996, 118, 2531–2532.

Curran, D. P.; Hadida, S.; HE, M. Thermal Allylations of Aldehydes with a Fluorous Allylstannane. Separation of Organic and Fluorous Products by Solid Phase Extraction with Fluorous Reverse Phase Silica Gel. J. Org. Chem. 1997, 62, 6714–6715.

Curran, D. P.; Luo, Z. Rapid Parallel Synthesis of Homoallylic Alcohols by Lewis Acid Mediated Allylations of Aldehydes with New Fluorous Allyl Stannanes. Med. Chem. Res. 1998, 8, 261–265.

Hadida, S.; Super, M. S.; Beckman, E. J.; Curran, D. P. Radical Reactions with Alkyl and Fluoroalkyl (Fluorous) Tin Hydride Reagents in Supercritical $CO_2$. J. Am. Chem. Soc. 1997, 119, 7406–7407.

Hoshino, M.; Degenkolb, P.; Curran, D. P. Palladium–Catalyzed Stille Couplings With Fluorous Tin Reactants. J. org. Chem. 1997, 62, 8341–8349.

* cited by examiner

Figure 1. A Schematic Illustration of the Use of a Fluorous Reaction Component in an Organic Transformation
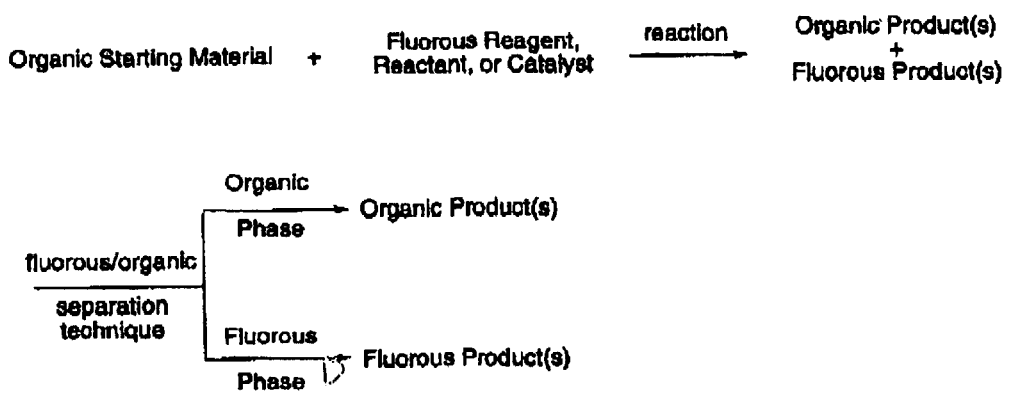

Figure 2. Illustrative Uses of Fluorous Tin Reagent $(C_6F_{13}CH_2CH_2)_3SnH$
Stiochiometric Use
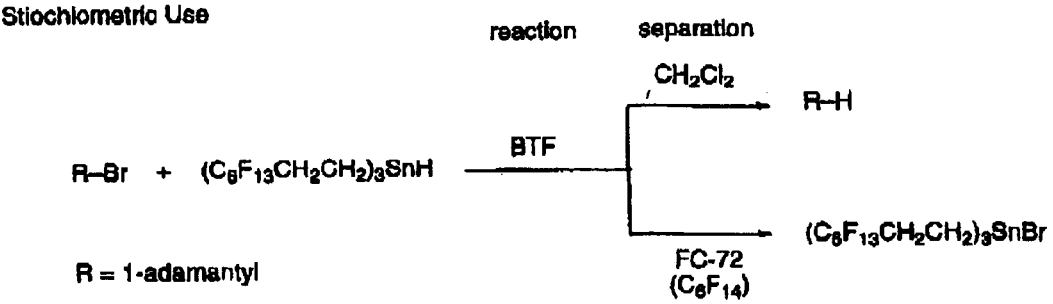
Catalytic Use
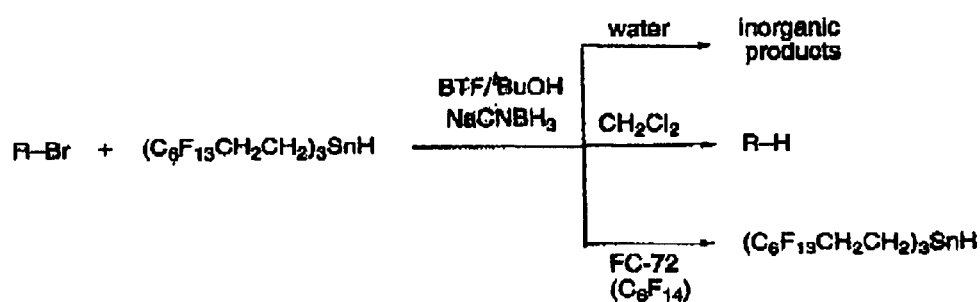

Figure 3. Representativ Syntheses of Fluorous Tin Reagents Bearing One Fluorous Chain
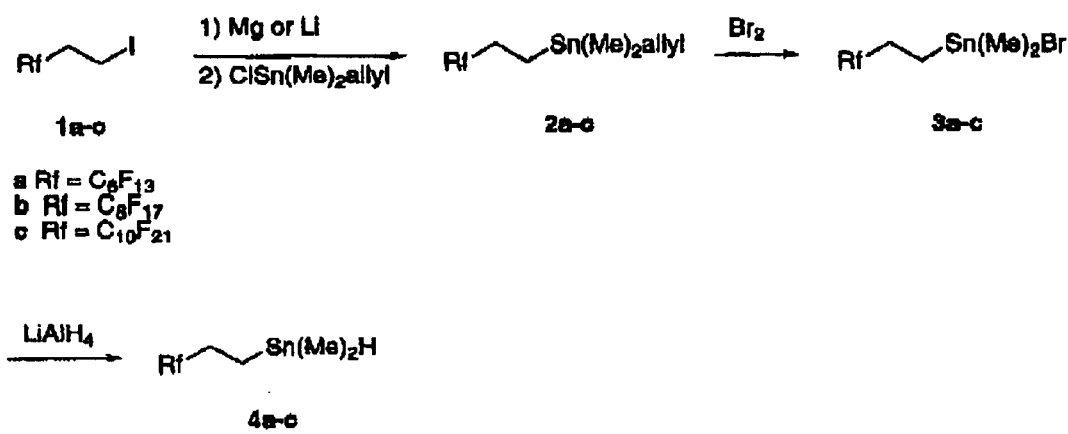

Figure 4. Representative Reactions of Fluorous Tin Reagents Bearing One Fluorous Chain.
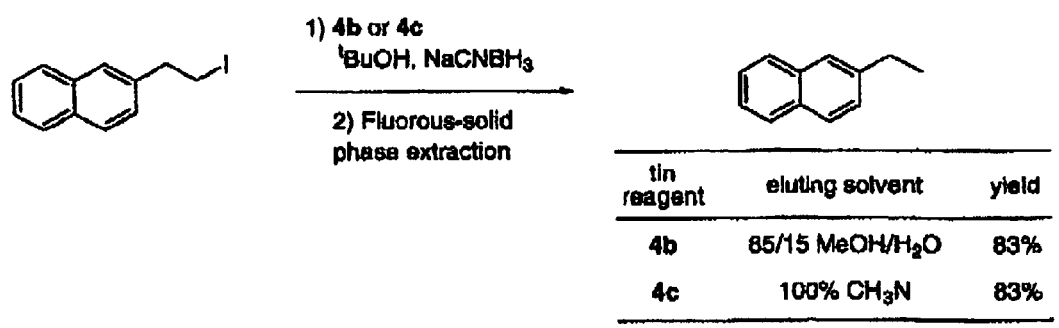

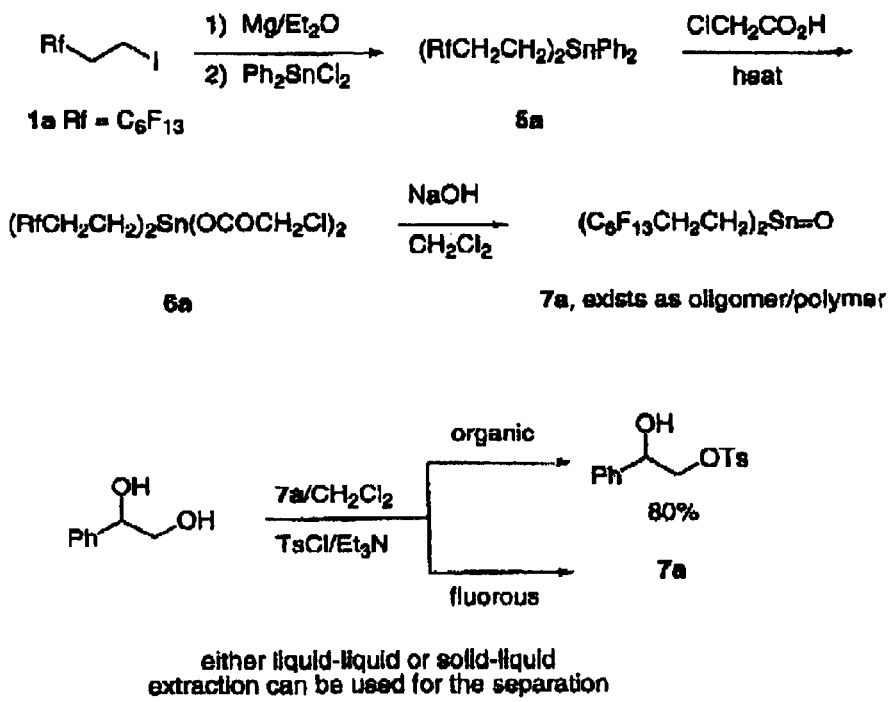
Figure 5. Synthesis and Use of Representative Fluorous Tin Reagents Bearing Two Fluorous Chains

FLUOROUS TIN COMPOUNDS AN METHODS OF USING FLUOROUS TIN COMPOUNDS

GOVERNMENTAL INTERESTS

This invention was made with government support under grant GM33372 awarded by the National Institutes of Health. The government has certain rights in this invention.

FIELD OF THE INVENTION

The present invention relates to fluorous tin compounds and to methods of using fluorous tin compounds, and, especially, to fluorous tin reaction components that are easily separated from non-fluorous compounds via fluorous separation techniques.

BACKGROUND OF THE INVENTION

Organic compounds are typically synthesized by reactions in which a starting material or reactant is contacted with one or more other reactants, reagents, or catalysts to form a new organic product. The separation of the desired products from any added reactants, reagents or catalysts (and/or from any byproducts derived from such reaction components) can be tedious and time consuming. Accordingly, improved methods for the separation of organic reaction products from other reaction components are needed.

Along these lines, the use of fluorous reagents, reactants and catalysts has recently begun to offer attractive new options. The use of such fluorous techniques is illustrated in general terms in FIG. 1. An organic (non-fluorous) starting material or reactant is contacted with a fluorous reactant, reagent or catalyst, possibly with other non-fluorous reaction components, and typically in a solvent, to form a new organic product or mixture of products. The organic product(s) are then separated from the unreacted fluorous reactant, reagent or catalyst and any other fluorous byproducts derived therefrom by simple fluorous-organic phase separation techniques such as liquid-liquid separation and/or solid-liquid separation. Such techniques have been described, for example, in U.S. Pat. Nos. 5,777,121 and 5,859,247, the disclosures of which are incorporated herein by reference.

Organotin reactants, reagents and catalysts are a powerful class of molecules that effect many useful transformations of organic starting materials or reactants to organic products. Accordingly, the use of organotin compounds is common practice in organic synthesis. See, for example, Davies, A. G. *Organotin Chemistry*; VCH: Weinheim, pp 327 (1997) and *Chemistry of Tin*; 2nd ed.; Smith, P. J., Ed.; Blackie: London, pp 578 (1997). However, the separation of the newly formed, non-tin containing organic products from the remaining tin compounds in the reaction mixture is notoriously difficult and improvements in separation techniques are needed to unlock the potential power of organic reactions mediated by organotin compounds.

Many of the most popular types of organotin reagents have the formula $R_3SnX$, where R is an alkyl group, often butyl, and X is a group which is involved in the reaction with an organic substrate. A few among many possible examples of such compounds include $Bu_3SnH$, $Bu_3SnN_3$, $Bu_3SnCl$ and $Bu_3SnPh$. Recently, fluorous analogs of these compounds have been introduced. The fluorous analogs are generally designed to accomplish reactions similar to the corresponding non-fluorous compound but to facilitate separation after reaction. In currently available fluorous tin reagents, each of the three alkyl groups R is replaced by a spacer group Rs attached to a fluorous group Rf according to the following general formula: $[(Rf)Rs)]_3SnX$. Examples of such fluorous tin reagents include $(C_6F_{13}CH_2CH_2)_3SnH$, $(C_6F_{13}CH_2CH_2)_3SnN_3$, $(C_6F_{13}CH_2CH_2)_3SnCl$, $(C_6F_{13}CH_2CH_2)_3SnPh$, etc.

Illustrative examples of the uses of one of these fluorous tin reagents, $(C_6F_{13}CH_2CH_2)_3SnH$, are shown in FIG. 2. Reduction of adamantyl bromide with 1 equiv of $(C_6F_{13}CH_2CH_2)_3SnH$ followed by fluorous-organic liquid-liquid extraction provides the organic product adamantane on evaporation of the organic liquid phase and the fluorous product $(C_6F_{13}CH_2CH_2)_3SnBr$ on evaporation of the fluorous phase. A similar reduction can be conducted in a more economical way by using a catalytic amount of the fluorous tin hydride along with an inexpensive inorganic reductant like sodium cyanoborohydride. A three-phase liquid extraction then provides the respective products: inorganic salts (from the aqueous phase), adamantane (from the organic phase), and the tin hydride catalyst (from the fluorous phase).

While currently available fluorous tin reagents provide advantages over the traditional (non-fluorous) trialkyltin class of reagents, some disadvantages remain that restrict the broad application thereof. For example, existing reagents with three fluorous chains can have low solubility in organic solvents. This low solubility can lead to problems in selecting suitable reaction solvents since it is often desirable that the tin compounds have substantial solubility under the reaction conditions. For example, the reactions in FIG. 2 require a non-standard solvent or co-solvent such as benzotrifluoride. Moreover, the large numbers of fluorines in currently available fluorous tin reagents result in compounds of high molecular weight, which is a detraction from the standpoint of expense and atom economy. Finally, certain classes of organotin reagents, for example $Bu_2SnO$, have fewer than three alkyl chains and cannot be rendered fluorous by current strategies.

It is thus very desirable to develop fluorous reaction compounds or components that substantially reduce or eliminate such problems.

SUMMARY OF THE INVENTION

The present invention provides fluorous tin reaction components (that is, reagents, reactants and/or catalysts) bearing only two or one fluorous groups or chains. Surprisingly, even though the fluorous reaction components of the present invention have many fewer fluorines than currently available fluorous reagents, the fluorous reaction components of the present invention can still be separated efficiently from organic (non-fluorous) reaction components by fluorous separation techniques. In addition, the fluorous tin reaction components of the present invention can be substantially more soluble in organic reaction solvents. Thus, the scope of application in chemical reactions of the fluorous tin reaction components of the present invention is dramatically increased without compromising the scope of separation. These features, coupled with lower molecular weight and increased atom economy, give the fluorous tin reaction components of the present invention significant advantages over currently available fluorous reagents.

In one aspect, the present invention provides a method of carrying out a reaction comprising the steps of:

mixing at least one organic reaction component with at least one fluorous reaction component having the formula:

$$X^1Sn(R)_n[Rs(Rf)]_{3-n}, X^1X^2Sn[Rs(Rf)]_2 \text{ or } O=Sn[Rs(Rf)]_2$$

wherein n is 1 or 2, R is a $C_1$–$C_6$ alkyl group, $X^1$ and $X^2$ are independently, the same or different, H, F, Cl, Br, I, $N_3$, $OR^1$, $OOR^1$ $SR^1$, $SeR^1$, CN, NC, $NR^1R^2$, an aryl group, a heteroaryl group, an alkyl group of 1 to 20 carbons, an alkenyl group, an alkynyl group, —C(O)$R^3$ (an acyl group), M((Rs') (Rf'))$_3$, OM((Rs')(Rf'))$_3$ or OOM((Rs')Rf'))$_3$, wherein M is Si, Ge, or Sn, and wherein $R^1$ and $R^2$ are each independently the same or different H, an alkyl group, —SO$_2$R$^3$ or —C(O) R$^3$, wherein $R^3$ is an alkyl group or an aryl group, and wherein Rs and Rs' are each independently the same or different a spacer group, and wherein Rf and Rf' are each independently the same or different a fluorous group;

carrying out a reaction to produce an organic product; and after producing the organic product, separating any excess of the fluorous reaction component and any fluorous byproduct of the fluorous reaction component using a fluorous separation technique.

As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons or perfluorocarbons, fluorohydrocarbons, fluorinated ethers and fluorinated amines). Fluorous compounds generally preferentially partition into a fluorous phase during fluorous-organic phase separation. For example, perfluorinated ether groups can have the general formula —[(CF$_2$)$_x$O(CF$_2$)$_y$]$_z$ CF$_3$, wherein x, y and z are integers. Perfluorinated amine groups can, for example, have the general formula —[(CF$_2$)$_x$ (NR$^a$)CF$_2$)$_y$]$_z$CF$_3$, wherein R$^a$ can, for example, be —(CF$_2$)$_n$ CF$_3$, wherein n is an integer. Fluorous ether groups and fluorous amine groups suitable for use in the present invention need not be perfluorinated, however. As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. A few examples of suitable fluorous groups Rf and Rf' for use in the present invention include, but are not limited to, —C$_4$F$_9$, —C$_6$F$_{13}$, —C$_8$F$_{17}$, —C$_{10}$, F$_{21}$, —C(CF$_3$)$_2$C$_3$F$_7$, —C$_4$F$_8$CF (CF$_3$)$_2$, —CF$_2$CF$_2$OCF$_2$CF$_2$OCF$_3$ and —CF$_2$CF$_2$(NCF$_3$) CF$_2$CF$_2$CF$_3$.

Perfluoroalkyl groups and hydrofluoroalkyl groups are well suited for use in the present invention. For example, Rf and Rf' can independently be a linear perfluoroalkyl group of 3 to 20 carbons, a branched perfluoroalkyl group of 3 to 20 carbons, and a hydrofluoroalkyl group of 3 to 20 carbons. Hydrofluoroalkyl groups preferably include up to one hydrogen atom for each two fluorine atoms. In the case of perfluoralkyl groups and hydrofluoroalkyl groups, Rf and Rf' are preferably a linear perfluoroalkyl group of 6 to 12 carbons, a branched perfluoroalkyl group of 6 to 12 carbons, or a hydrofluoroalkyl group of 6 to 12 carbons.

In another aspect, the present invention provides a chemical compound of the formula $$X^1Sn(R)_n[Rs(Rf)]_{3-n},$$

wherein n is 1 or 2, R is a $C_1$–$C_6$ alkyl group, $X^1$ is H, F, Cl, Br, I, $N_3$, $OR^1$, $OOR^1$ $SR^1$, $SeR^1$, CN, NC, $NR^1R^2$, an aryl group, a heteroaryl group, an alkyl group of 1 to 20 carbons, an alkenyl group, an alkynyl group, —C(O)$R^3$, M((Rs') (Rf'))$_3$, OM((Rs')(Rf'))$_3$ or OOM((Rs')Rf'))$_3$, wherein M is Si, Ge, or Sn, and wherein $R^1$ and $R^2$ are each independently the same or different H, an alkyl group, —SO$_2$R$^3$ or —C(O) R$^3$, wherein $R^3$ is an alkyl group or an aryl group, and wherein Rs and Rs' are each independently the same or different an alkylene group of 1 to 6 carbons or a phenylene group, and wherein Rf and Rf' are each independently a fluorohydrocarbon group, a perfluorocarbon group, a fluorinated ether group or a fluorinated amine group.

In another aspect, the present invention provides chemical compound having the formula:

$$O=Sn[Rs(Rf)]_2$$

wherein Rs is an alkylene group of 1 to 6 carbons or a phenylene group and wherein Rf is a fluorohydrocarbon group, a perfluorocarbon group, a fluorinated ether group or a fluorinated amine group. Such molecules can exist as oligomers or polymers with the formula (O=Sn[Rs(Rf)]$_2$)$_n$.

In still a further aspect, the present invention provides a chemical compound having the formula:

$$X^1X^2Sn[Rs(Rf)]_2$$

wherein $X^1$ and $X^2$ are independently, the same or different, H, $N_3$, $OR^1$, $OOR^1$ $SR^1$, $SeR^1$, CN, NC, $NR^1R^2$, a heteroaryl group, an alkyl group of 2 to 20 carbons, an alkenyl group, an alkynyl group, —COR$^3$, M((Rs')(Rf'))$_3$, OM((Rs')(Rf'))$_3$ or OOM((Rs')Rf'))$_3$, wherein M is Si, Ge, or Sn, and wherein $R^1$ and $R^2$ are each independently the same or different H, an alkyl group, —SO$_2$R$^3$ or —COR$^3$, wherein $R^3$ is an alkyl group or an aryl group, wherein Rs and Rs' are each independently the same or different an alkylene group of 1 to 6 carbons or a phenylene group, and wherein Rf and Rf' are each independently a fluorohydrocarbon group, a perfluorocarbon group, a fluorinated ether group or a fluorinated amine group.

In several embodiments, $X^1$ and/or $X^2$ are (independently), for example, an allyl group, Br, F, Cl, I or H. In several other embodiments, Rs is an alkylene group (preferably, —CH$_2$CH$_2$—), and/or Rf is a perfluoroalkyl group.

Separation of the fluorous reaction components of the present invention and any fluorous byproducts thereof from organic products and other organic compounds is achieved by using fluorous separation techniques that are based upon differences between/among the fluorous nature of a mixture of compounds. As used herein, the term "fluorous separation technique" refers generally to a method that is used to separate mixtures containing fluorous molecules or organic molecules bearing fluorous domains from each other and/or from non-fluorous compounds based predominantly on differences in the fluorous nature of molecules (for example, size and/or structure of a fluorous molecule or domain or the absence thereof). Fluorous separation techniques include but are not limited to solid phase extraction or chromatography over solid fluorous phases such as fluorocarbon bonded phases or fluorinated polymers. See, for example, Danielson, N. D. et al., "Fluoropolymers and Fluorocarbon Bonded Phases as Column Packings for Liquid Chromatography," *J. Chromat.*, 544, 187–199 (1991) and Curran, D. P.; Hadida, S.; He, M. *J. Org. Chem.* 62, 6714 (1997). Examples of suitable fluorocarbon bonded phases include commercial Fluofix® and Fluophase™ columns available from Keystone Scientific, Inc. (Bellefonte, Pa.), and FluoroSep™-RP-Octyl from ES Industries (Berlin, N.J.). Other fluorous separation techniques include liquid-liquid based separation methods such as liquid-liquid extraction or countercurrent distribution with a fluorous solvent and an organic solvent.

The terms "alkyl", "aryl", and other groups refer generally to both unsubstituted and substituted groups unless specified to the contrary. Unless otherwise specified, alkyl groups are hydrocarbon groups and are preferably $C_1$–$C_{15}$ (that is, having 1 to 15 carbon atoms) alkyl groups, and more preferably $C_1$–$C_{10}$ alkyl groups, and can be branched or unbranched, acyclic or cyclic. The above definition of an alkyl group and other definitions apply also when the group is a substituent on another group. The term "aryl" refers generally to an unsubstituted or substituted phenyl (Ph) group or napthyl group.

The term "heteroaryl group" refers generally to an aromatic ring of five or six atoms in which one or more of the atoms is oxygen, nitrogen, or sulfur. The heteroaryl groups or rings can be substituted or unsubstituted and can be isolated or fused to benzo rings. Examples of isolated heteraryl rings include, but are not limited to, furan rings. Examples of benzo-fuzed heteraryl ring include, but are not limited to, benzofurans.

The term "alkenyl" refers generally to a straight or branched chain hydrocarbon group with at least one double bond, preferably with 2–15 carbon atoms, and more preferably with 3–10 carbon atoms (for example, —CH=CHR$^c$ or —CH$_2$CH=CHR$^c$, wherein R$^c$ is, for example, H or an alkyl group). The term "alkynyl" refers generally to a straight or branched chain hydrocarbon group with at least one triple bond, preferably with 2–15 carbon atoms, and more preferably with 3–10 carbon atoms (for example, —C≡CR$^c$ or —CH$_2$C≡CR$^c$). The term "alkylene" refers generally to bivalent forms of an alkyl group. The term "phenylene group" refers generally to bivalent forms of an a phenyl group (—C$_6$H$_4$—) wherein the two groups attached thereto are situated ortho, meta or para.

The groups set forth above, can be substituted with a wide variety of substituents. For example, alkyl and alkylene groups can preferably be substituted with a group or groups including, but not limited to, halide(s), alkenyl groups, alkynyl and aryl groups. Aryl groups and heteroaryl groups can preferably be substituted with a group or groups including, but not limited to, halide(s), alkyl group(s), cyano group(s) and nitro group(s). As used herein, the terms "halide" or "halo" refer to fluoro, chloro, bromo and iodo. Preferred halide substituents are F and Cl.

BRIEF DESCRIPTION OF THE DRAWINGS

FIG. 1 illustrates use of fluorous reagents in organic synthesis.

FIG. 2 illustrates an example of use of the fluorous tin reagent (C$_6$F$_{13}$CH$_2$CH$_2$)SnH in the reduction of adamantyl bromide.

FIG. 3 illustrates an example of synthesis of fluorous tin reagents of the present invention bearing one fluorous group.

FIG. 4 illustrates a series of reactions with fluorous tin reagents of the present invention.

FIG. 5 illustrates an example of synthesis of fluorous tin reagents of the present invention bearing two fluorous groups.

DETAILED DESCRIPTION OF THE INVENTION

The fluorous tin reagents of the present invention can generally be made by modification of reactions known to those skilled in the art of organotin chemistry. See, for example, Davies, A. G. *Organotin Chemistry*; VCH: Weinheim, pp 327 (1997) and *Chemistry of Tin*; 2nd ed.; Smith, P. J., Ed.; Blackie: London, pp 578 (1997). For example, Grignard reagents such as Rf(CH$_2$)$_n$MgI, organolithium reagents Rf(CH$_2$)$_n$Li, or related organometallic reagents can be reacted with known tin electrophiles Y$_2$Sn (X)R to give (Rf(CH$_2$)$_n$)$_2$Sn(X)R. In tin reagent Y$_2$Sn(X)R, Y is a leaving group. There are many types of leaving groups known to those skilled in the art and examples of some of the preferred groups Y for the current invention are chloride, bromide or triflate. In another approach, alkenes such as Rf(CH$_2$)$_{n-2}$CH=CH$_2$ can be hydrostannated with H$_2$Sn (X)R via radical or metal catalyzed reactions to give (Rf (CH$_2$)$_n$)$_2$Sn(X)R.

The interchange of groups X in (Rf(CH$_2$)$_n$)$_2$SnRX for other groups X is well known to those skilled in the art and can be accomplished by large classes of reactions wherein a nucleophilic precursor of the product X group (for example, cyanide, azide, alkoxide, RMgBr, etc.) replaces the leaving group X (for example a halogen or a triflate, etc.) in the tin precursor (for example, stannylation of an alcohol), by reactions wherein a tin nucleophile (X=metal) adds to or substitutes an electrophilic precursor of the product X group (for example, allylation of a tin metal reagent with an allyl halide), by reactions wherein the Sn—X bond adds to a multiple bond (for example, hydrostannation of a carbon-carbon or carbon-oxygen double bond), or by reactions involving electrophilic cleavage of an Sn—X bond (for example, conversion of a tin hydride or vinyl or aryl tin to a tin bromide by reaction with dibromine). Other types of reactions to exchange X groups, including metal catalyzed reactions such as Stille and related couplings, are also used.

Analogous transformations are possible starting from YSn(R)$_2$X or HSn(R)$_2$X to make Rf(CH$_2$)$_n$SnR$_2$X reagents. Examples that illustrative a few of the many possibilities are shown in FIG. 3. Fluorous iodides 1a–c were converted to appropriate organometallic derivatives, which were in turn reacted with allyldimethyltin to give the new tin reagents 2a–c bearing one fluorous chain. These fluorous allyltin reagents can be used for the allylation of various organic molecules such as aldehydes under standard reaction conditions. They can also be used to make other fluorous tin reagents. For example, reaction of 2a–c with dibromine generated tin bromides 3a–c. These tin bromides can be reacted with a wide range of nucleophiles to make other new fluorous tin reagents. In the example of FIG. 3, tin bromides were reacted with lithium aluminum hydride to make the tin hydrides 4a–c.

Some of the advantages of the fluorous tin reagents of the present invention are illustrated by the series of reactions of FIG. 4. Reduction of napthyl ethyl iodide with tin hydrides 4b and 4c under the standard conditions, followed by rapid solid phase extraction over fluorous reverse phase silica gel, provided pure 2-ethyladamantane in a simple and effective reaction and separation process. This simple separation compares very favorably to the use of the standard reagent Bu$_3$SnH, which requires careful chromatographic separation or application of some other specialized separation technique. Moreover, the currently available fluorous reagent (C$_6$F$_{13}$CH$_2$CH$_2$)$_3$SnH is not expected to form the product efficiently under these conditions because it is insoluble or nearly insoluble in t-butanol. A suitable solvent or cosolvent like benzotrifluoride is be needed in that case.

An example of a fluorous tin reagent bearing two fluorous chains is (C$_6$F$_{13}$CH$_2$CH$_2$)$_2$SnO, for which a synthetic route is shown in FIG. 5. The synthetic route of FIG. 5 modifies an approach reported synthesis of Bu$_2$SnO, and like the standard alkyl tin oxide, the fluorous alkyltin oxide is not monomeric but instead appears to exists as oligomers and/or polymers. See Kong, X.; Grindley, B.; Bakshi, P. K.; Cameron, T. S. *Organometallics*. 12, 4881 (1993). Reaction of the Grignard reagent derived from 1a in suitable stoichiometry gave the bis-phenyltin reagent 5a, which was converted to the bis-chloroacetate 6a. Exposure of this reagent to hydroxide gave the tin oxide 7a.

Among other uses, the mono-functionalization of diols is one of the most popular applications of $Bu_2SnO$. Martinelli and coworkers have recently introduced a catalytic variant of the traditional stoichiometric procedure, but the tin catalyst must still be separated from the desired organic product. See Martinelli, M. J., et al. *Org. Lett.*, 1, 447 (1999). As shown in FIG. 5, the tin oxide reaction components of the present invention can also be used to catalyze the mono-tosylation of diols under the conditions reported by Martinelli. No fluorinated reaction solvent or cosolvent is needed. Simple purification of the crude reaction mixture by liquid-liquid extraction or solid-liquid extraction provided the pure organic tosylate (organic phase) separate from the recovered tin oxide 7a (fluorous phase). The recovered tin oxide 7a can be reused.

EXPERIMENTAL

Example 1a

Allyl-dimethyl-(3,3,4,4,5,5,6,6,7,7,8,8,8-tridecafluorooctyl)stannane (2a). Freshly prepared allyldimethyltin chloride (2.86 g, 12.7 mmol) was added dropwise to the Grignard reagent of $C_6F_{13}CH_2CH_2MgI$, which was prepared from $C_6F_{13}CH_2CH_2I$ (6.0 g, 12.7 mmol) and magnesium powder (0.37 g, 15.2 mmol). The reaction mixture was refluxed overnight (16 h) before quenching with 1N HCl. The crude product was purified by vacuum distillation (112° C./water pump) to give pure 2a as a colorless oil (3.20 g, 35%). $^1$H NMR (CDCl$_3$) δ 5.95–5.86 (m, 1H), 4.85–4.80 (dd, J=16.8, 1.4 Hz, 1H), 4.73–4.69 (dd, J=11.8, 1.8 Hz, 1H), 2.30–2.12 (m, 2H), 1.83 (d, J=8.5 Hz, 2H), 1.00–0.92 (m, 2H), 0.15 (s, $J_{Sn-H}$=26.3 Hz, 6H); $^{13}$C NMR (CDCl$_3$) δ 136.8, 121.8–107.2 (m), 27.9 (t), 16.9, –1.8, –12.2; $^{19}$F NMR (CDCl$_3$) δ –81.3 (3F), –117.2 (2F), –122.5 (2F), –123.4 (2F), –123.9 (2F), –126.7 (2F); $^{119}$Sn NMR (C$_6$D$_6$): δ –1.4; HRMS: calc. 496.9597 (M$^+$-Me), found: 496.9583. IR (thin film): 1626 cm$^{-1}$.

Example 1b

Allyl-dimethyl-(3,3,4,4,5,5,6,6,7,7,8,8,9,9,10,10,10-heptadecafluorodecyl)stannane (2b). To a solution of $C_8CF_{17}CH_2CH_2I$ (3.34 g, 5.82 mmol) in dry ether (50 mL) and dry hexanes (50 mL) at –78° C. was added $^t$BuLi (7.5 mL, 1.7 M in pentane). After stirring at –78° C. for 30 min, freshly prepared allyldimethyl tinchloride (1.46 g, 6.47 mmol) was added slowly. The reaction mixture was stirred at –78° C. for 1 h and allowed to warm to room temperature in two to three hours before quenching with water. After extraction between ether and water, the ether phase was dried over MgSO$_4$. The crude product was purified by flash chromatography with n-heptane to give 2b as a clear oil (2.15 g, 58%). $^1$H NMR (CDCl$_3$) δ 5.95–5.86 (m, 1H), 4.85–4.69 (dd, J=17.0, 1.1 Hz, 2H), 2.30–2.12 (m, 2H), 1.83 (d, J=8.7 Hz, 2H), 1.00–0.92 (m, 2H), 0.15 (s, $J_{Sn-H}$=26.1 Hz, 6H); $^{13}$C NMR (CDCl$_3$) δ 136.8, 119.2–108.2 (m), 28.0 (t), 17.1, –1.6; $^{19}$F NMR (CDCl$_3$) δ –81.0 (3F), –116.9 (2F), –122.2 (6F), –122.3 (2F), –123.6 (2F), –126.3 (2F); $^{119}$Sn NMR (C$_6$D$_6$) δ –1.39; HRMS: calcd. 622.9690 (M$^+$-Me), found: 622.9685; IR (thin film): 1626 cm$^{-1}$.

Example 1c

Allyl-dimethyl-(3,3,4,4,5,5,6,6,7,7,8,8,9,9,10,10,11,11,12,12,12-heneicosafluorododecyl)stannane (2c). This compound was prepared with the same procedure as for 2b. Yield: 83% (clear oil). $^1$H NMR (CDCl$_3$) δ 5.98–5.83 (m, 1H), 4.87–4.80 (dd, J=16.6, 1 Hz, 1H), 4.74–4.70 (dd, J=9.6, 1 Hz, 1H), 2.30–2.12 (m, 2H), 1.83 (d, J=8.6 Hz, 2H), 1.00–0.94 (m, 2H), 0.15 (s, $J_{Sn-H}$=26.1 Hz, 6H); $^{13}$C NMR (CDCl$_3$) δ 136.8, 121.9–106.9 (m), 28.0 (t), 17.1, –1.6, –11.8; $^{19}$F NMR (CDCl$_3$) δ –80.9 (3F), –116.9 (2F), –122.0 (10F), –122.9 (2F). –123.6 (2F), –126.3 (2F); $^{119}$Sn NMR (C$_6$D$_6$) δ –0.47; HRMS: Calcd. 722.9626 (M$^+$-Me), found: 722.9623; IR (thin film): 1626 cm$^{-1}$.

Example 2a

Dimethyl-(3,3,4,4,5,5,6,6,7,7,8,8,8-tridecafluorooctyl)stannane (4a). Br$_2$ (0.43 g, 2.68 mmol) was added to a solution of 2a (1.20 g, 2.23 mmol) in dry ether (10 mL) at 0° C. The brown reaction mixture was further stirred at room temperature for 1.5 h. After evaporation of solvent, the residue was partitioned between CH$_2$Cl$_2$ and FC-72. The CH$_2$Cl$_2$ phase was further washed with FC-72 for three times. The crude tin bromide 3a was dissolved in dry ether (10 mL) and cooled to –78° C., to which LAH (2.1 mL, 1.0 M in ether) was added. The reaction was quenched with water after stirring at –78° C. for three hours. The crude mixture was further purified by column chromatography with heptane to give 4a as a clear oil (0.72 g, 65% for two steps). $^1$H NMR (C$_6$D$_6$) δ 4.75 (s, 1H), 2.03–1.85 (m, 2H), 0.78–0.60 (m, 2H), –0.7 (s, $J_{Sn-H}$=17.2 Hz, 6H); $^{13}$C NMR (C$_6$D$_6$) δ 122.2–107.5 (m), 28.5 (t), –3.0, –13.4; $^{19}$F NMR (CDCl$_3$) δ –81.2 (3F), –117.1 (2F), –122.4 (2F), –123.4 (2F), –123.9 (2F), –126.6 (2F); $^{119}$Sn NMR (C$_6$D$_6$) δ –86.8; HRMS: calcd. 496.9597, found: 496.9563. IR (thin film): 1839 cm$^{-1}$.

Example 2b

Dimethyl-(3,3,4,4,5,5,6,6,7,7,8,8,9,9,10,10,10-heptadecafluorodecyl)stannane (4b). This compound was prepared with the same procedure as for 4a. Overall yield for two steps: 53% (clear oil). $^1$H NMR (C$_6$D$_6$) δ 4.74 (s, 1H), 2.03–1.85 (m, 2H), 0.72–0.66 (m, 2H), –0.07 (s, $J_{Sn-H}$=28.2 Hz, 6H); $^{13}$C NMR (C$_6$D$_6$) δ 120.0–108.4 (m), 29.3 (t), –2.4, –12.8; $^{19}$F NMR (CDCl$_3$) δ –81.1 (3F), –116.3 (2F), –121.8 (6F), –122.9 (2F), –123.3 (2F), –126.3 (2F); $^{119}$Sn NMR (C$_6$D$_6$) δ –86.8; HRMS: calcd. 596.9533, found: 596.9543. IR (thin film): 1841 cm$^{-1}$.

Example 2c

Dimethyl-(3,3,4,4,5,5,6,6,7,7,8,8,9,9,10,10,11,11,12,12,12-heneicosafluorododecyl)stannane (4c). This compound was prepared with the same procedure as for 4a. Overall yield for two steps: 85% (clear oil). $^1$H NMR (C$_6$D$_6$) δ 4.75 (s, 1H), 2.05–1.87 (m, 2H), 0.73–0.67 (m, 2H), –0.07 (s, $J_{Sn-H}$=28.1 Hz, 6H); $^{13}$C NMR (C$_6$D$_6$) δ 120.3–108.2 (m), 29.2 (t), –2.4, –12.5; $^{19}$F NMR (CDCl$_3$): δ –81.2 (3F), –114.7 (2F), –121.9 (10F), –122.4 (2F), –122.9 (2F), –126.9 (2F); $^{119}$Sn NMR (C$_6$D$_6$) δ –86.9; HRMS: calcd. 696.9469 found: 696.9462. IR (thin film): 1840 cm$^{-1}$.

Example 3

Measurement of the Partition Coefficient of Fluorous Tin hyrides 4a–c. Fluorous tin hydrides (2–12 mg) were stirred with FC-72 (1 mL) and benzene (2 mL) or acetonitrile (1 mL) for 10 min. After separation, n-octadecane was added to both phases as an internal standard (for FC-72 phase, the solvent was evaporated and ethyl acetate (1 mL) was added to dissolve both the tin hydride and n-ocadecane). An aliquot (10 uL) of each phase was injected to GC for three times and the relative peak area was used to calculate the following partition coefficients of tin hydrides: FC-72/CH3CN, 4a, 2.4; 4b, 14; 4c, 48; FC-72/benzene, 4a, 0.7; 4b, 2.5; 4c, 4.7.

Example 4

General Procedure for the Reduction of 2-(2-iodoethyl) naphthalene with Fluorous Tin Hydrides. The iodide (0.5 mmol), fluorous tin hydride (0.05 mmol) and sodium cyanoborohydride (0.75 mmol) were suspended in tert-butanol (0.1–0.15 M for iodide). After flushing 5 min with argon, the reaction mixture was irradiated with a sunlamp overnight. After removal of solvent by evaporation, the residue was extracted with ether and water. The ether phase was dried and passed through a short column of fluorous reverse phase silica gel (bonded phase —OSi(Me)$_2$CH$_2$CH$_2$C$_6$F$_{13}$) eluting with acetonitrile or 85/15 methanol/water. The organic fraction was evaporated and analyzed by proton NMR spectroscopy.

Example 5

Bis(perfluorohexylethyl)diphenyltin (5a).

In a dry round bottom flask, anhydrous ether (10 ml) was added to Mg (0.40 g, 16.37 mmol). Under nitrogen, perfluorohexylethyl iodide 1a (0.517 g, 1.09 mmol) was added dropwise, and the flask was sonicated for 30 min. The rest of the perfluorohexylethyl iodide (4.65 g, 9.89 mmol) was added slowly over 5 min, and the mixture was refluxed for 2 h, during which the mixture turned dark green. After 2 h, a solution of diphenyltin dichloride (1.50 g, 4.36 mmol) in benzene (15 ml) was added via a cannula. The resulting mixture was refluxed for 4 h with stirring. The mixture was cooled and quenched with 1M HCl (2×5 ml) and sat. NH$_4$Cl (2×30 ml). The organic layer was dried over MgSO$_4$. Removal of solvent yielded a mixture of 3.68 g of a brown amorphous solid. $^1$H NMR analysis showed it to be 7/1 mixture of bis(perfluorohexylethyl)diphenyltin 5a and diner (C$_6$F$_{13}$CH$_2$CH$_2$)$_2$: $^1$H NMR (300 MHz, CDCl$_3$) δ 1.41–1.47 (t, 4H), 2.07–2.18 (t, 4H), 2.25–2.40 (m, 4H), 7.38–7.44 (m, 10H). $^{19}$F NMR (282 MHz, CDCl$_3$ with CFCl$_3$): δ –126.69, –123.85, –123.42, –122.49, –117.00, –114.91, –81.32.

Example 6

Bis(perfluorohexylethyl)tin bis(chloroacetate) (6a).

In a round bottom flask, the mixture of 5a and dimer (2.28 g, 2.36 mmol) and chloroacetic acid (0.45 g, 4.72 mmol) were combined. The mixture was heated to 160° C. for 20 min. A white precipitate formed on cooling. Hexanes (25 ml) were added, and the mixture was refluxed until the precipitate dissolved. After cooling, the residue was filtered, and yielded 1.68 g (73%) bis(perfluorohexylethyl)tin bis (chloroacetate) 6a: $^1$H NMR (300 MHz, CDCl$_3$): δ 1.67–1.93 (t, 4H), 2.46–2.57 (m, 4H), 4.16 (s, 4H); $^{19}$F NMR (282 MHz, CDCl$_3$): δ –126.69, –123.78, –123.43, –122.46, –116.55, –81.30.

Example 7

Bis(perfluorohexylethyl)tin Oxide (7a).

In a round bottom flask 6a (0.1 g, 0.11 mmol) was taken up in ether (5 ml). 2.5M NaOH (0.132 ml, 0.33 mmol) was added, and the mixture was stirred for 1 h. Hexanes (20 ml) was added and the resulting mixture was transferred to a separatory funnel. The mixture was washed with sat. 1N HCl (2×5 ml) and NH$_4$Cl (2×20 ml). The organic layer was dried over MgSO$_4$. Removal of solvent yielded 0.34 g (76%) bis(perfluorohexylethyl)tin oxide 7a: $^1$H NMR (300 MHz, acetone-d$_6$): δ 2.50–2.61 (broad band, 4H), 2.77–2.84 (t, 4H); $^{19}$F NMR (282 MHz, acetone-d$_6$ with CFCl$_3$): δ –125.69, –122.84, –122.35, –121.37, –115.17, –80.56; $^{119}$Sn NMR (111.8 MHz, CDCl$_3$ with (CH$_3$)$_4$Sn): δ –167.23.

Example 8

General Procedure for Catalyzed Tosylation of 1-phenyl-1,2-ethane diol.

In a round bottom flask, 1-phenyl-1,2-ethane diol (1 mmol) was dissolved in CH$_2$Cl$_2$ (5 ml). Triethylamine (1 mmol) and tin oxide 7a (0.02 mmol) were added. Tosyl chloride was added and the solution was stirred for 50 min. After addition of H$_2$O (1 ml), the mixture was transferred to a separatory funnel. The aqueous layer was washed with dicholormethane (2×10 ml). The combined organic layers were was with H$_2$O (2×25 ml) and brine (2×25 ml). The organic layer was dried over MgSO$_4$. Removal of solvent yielded a mixture of toluene-4-sulfonic acid-2-hydroxy-2-phenyl ethyl ester and tin oxide 7a. The mixture can be separated by either liquid-liquid or solid-liquid extraction.

Procedure for Liquid-liquid Extraction with FC-72.

A mixture of toluene-4-sulfonic acid-2-hydroxy-2-phenyl ethyl ester and tin oxide 7a was taken up in dichloromethane (25 ml) and transferred to a separatory funnel. The resulting mixture was washed with FC-72 (8×25 ml). The dichloromethane was evaporated to yield toluene-4-sulfonic acid-2-hydroxy-2-phenyl ethyl ester and the FC-72 was evaporated to yield 7a.

Prodedure for Solid Phase Extraction with Fluorous Silica Gel.

A mixture of toluene-4-sulfonic acid-2-hydroxy-2-phenyl ethyl ester and tin oxide 7a was taken up in a mixture of 9/1 methanol:water. The resulting mixture was transferred to a column containing fluorous reverse phase silica gel (bonded phase —OSi(Me)$_2$CH$_2$CH$_2$C$_6$F$_{13}$) (100 Mg). The column was then washed with a mixture of 9/1 methanol:water (3 ml), followed by THF (3 ml). Evaporation of the methanol:water mixture yielded toluene-4-sulfonic acid-2-hydroxy-2-phenyl ethyl ester.

Although the present invention-has been described in detail in connection with the above examples, it is to be understood that such detail is solely for that purpose and that variations can be made by those skilled in the art without departing from the spirit of the invention except as it may be limited by the following claims.

What is claimed is:

1. A method of carrying out a reaction comprising the steps of:

mixing at least one organic reaction component with a fluorous reaction component having the formula:

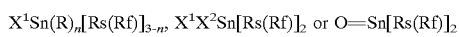

$X^1Sn(R)_n[Rs(Rf)]_{3-n}$, $X^1X^2Sn[Rs(Rf)]_2$ or $O=Sn[Rs(Rf)]_2$ wherein n is 1 or 2, R is a C$_1$–C$_6$ alkyl group, X$^1$ and X$^2$ are independently, the same or different, H, F, Cl, Br, I, N$_3$, OR$^1$, OOR$^1$, SR$^1$, SeR$^1$, CN, NC, NR$^1$R$^2$, an aryl group, a heteroaryl group, an alkyl group of 1 to 20 carbons, an alkenyl group, an alkynyl group, —C(O) R$^3$, M((Rs')(Rf'))$_3$, OM((Rs')(Rf'))$_3$ or OOM((Rs') Rf'))$_3$, wherein M is Si, Ge, or Sn, and wherein R$^1$ and R$^2$ are each independently the same or different H, an alkyl group, —SO$_2$R$^3$ or —C(O)R$^3$, wherein R$^3$ is an alkyl group or an aryl group, and wherein Rs and Rs' are each independently the same or different a spacer group, and wherein Rf and Rf' are each independently the same or different a fluorous group;

carrying out a reaction to produce an organic product; and after producing the organic product, separating any excess of the fluorous reaction component and any fluorous byproduct of the fluorous reaction component using a fluorous separation technique.

2. The method of claim 1 wherein $X^1$ and $X^2$ are independently the same or different an allyl group, Br, Cl, F, I, or H, Rs is —CH$_2$CH$_2$—, and Rf is a perfluoroalkyl group.

3. The method of claim 1 wherein Rf is a fluorohydrocarbon group, a perfluorocarbon group, a fluorinated ether group or a fluorinated amine group.

4. The method of claim 1 wherein Rf is a linear perfluoroalkyl group of 3 to 20 carbons, a branched perfluoroatkyl group of 3 to 20 carbons, or a hydrofluoroalkyl group of 3 to 20 carbons, the hydrofluoroalkyl group comprising up to one hydrogen atom for each two fluorine atoms.

5. The method of claim 1 wherein Rf is a linear perfluoroalkyl group of 6 to 12 carbons, a branched perfluoroalkyl group of 6 to 12 carbons, or a hydrofluoroalkyl group of 6 to 12 carbons, the hydrofluoroalkyl group comprising up to one hydrogen atom for each two fluorine atoms.

6. The method of claim 1 wherein Rf is a perfluoroalkyl group.

7. The method of claim 1 wherein Rs is an alkylene group or a phenylene group.

8. The method of claim 1 wherein Rs is an alkylene group.

9. A method for carrying out a chemical reaction, comprising the steps of:

combining at least one fluorous reaction component having the formula:

(X$^1$Sn(R)$_n$[Rs(Rf)]$_{3-n}$, X$^1$X$^2$Sn[Rs(Rf)]$_2$ or O=Sn[RS(Rf)]$_2$ wherein n is 1 or 2, R is a C$_1$–C$_6$ alkyl group, X$^1$ and X$^2$ are independently, the same or different, H, F, Cl, Br, I, N$_3$, OR$^1$, OOR$^1$ SR$^1$, SeR$^1$, CN, NC, NR$^1$R$^2$, an aryl group, a heteroaryl group, an alkyl group of 1 to 20 carbons, an alkenyl group, an alkynyl group, —C(O)R$^3$, M((Rs')(Rf'))$_3$, OM ((Rs')(Rf'))$_3$ or OOM((Rs')Rf'))$_3$, wherein M is Si, Ge, or Sn, and wherein R$^1$ and R$^2$ are each independently the same or different H, an alkyl group, —SO$_2$R$^3$ or —C(O)R$^3$, wherein R$^3$ is an alkyl group or an aryl group, and wherein Rs and Rs' are each independently the same or different a spacer group, and wherein Rf and Rf' are each independently the same or different a fluorous group, and at least one organic reaction component convertible in the presence of the fluorous reaction component to a product in an organic solvent;

contacting the fluorous reaction component and the organic reaction component in the organic solvent under conditions suitable to produce the product; and after production of the product, separating any excess of the fluorous reaction component and any fluorous byproduct of the fluorous reaction component using a fluorous separation technique.

10. A chemical compound having the formula:

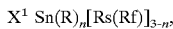

X$^1$ Sn(R)$_n$[Rs(Rf)]$_{3-n}$, wherein n is 1 or 2, R is a C$_1$–C$_6$ alkyl group, X$^1$ is H, F, Cl, Br, I, N$_3$, OR$^1$, OOR$^1$ SR$^1$, SeR$^1$, CN, NC, NR$^1$R$^2$, an aryl group, a heteroaryl group, an alkyl group of 1 to 20 carbons, an alkenyl group, an alkynyl group, —C(O)R$^3$, M((Rs')(Rf'))$_3$, OM((Rs')(Rf'))$_3$ or OOM((Rs')Rf'))$_3$, wherein M is Si, Ge, or Sn, and wherein R$^1$ and R$^2$ are each independently the same or different H, an alkyl group, —SO$_2$R$^3$ or —C(O) R$^3$, wherein R$^3$ is an alkyl group or an aryl group, and wherein Rs and Rs' are each independently the same or different an alkylene group of 1 to 6 carbons or a phenylene group, wherein Rf is a fluorohydrocarbon group of at least 3 carbons, a perfluorocarbon group of at least 3 carbons, a fluorinated ether group or a fluorinated amine group, and wherein Rf' is a fluorohydrocarbon group, a perfluorocarbon group, a fluorinated ether group or a fluorinated amine group.

11. The compound of claim 10 wherein X$^1$ is an allyl group, Br, Cl, F, I, or H, Rs is —CH$_2$CH$_2$—, and Rf is a perfluoroalkyl group.

12. The compound of claim 10 wherein Rf is a fluorohydrocarbon group, a perfluorocarbon group, a fluorinated ether group or a fluorinated amine group.

13. The compound of claim 10 wherein Rf is a linear perfluoroalkyl group of 3 to 20 carbons, a branched perfluoroalkyl group of 3 to 20 carbons, or a hydrofluoroalkyl group of 3 to 20 carbons, the hydrofluoroalkyl group comprising up to one hydrogen atom for each two fluorine atoms.

14. The compound of claim 10 wherein Rf is a linear perfluoroalkyl group of 6 to 12 carbons, a branched perfluoroalkyl group of 6 to 12 carbons, or a hydrofluoroalkyl group of 6 to 12 carbons, the hydrofluoroalkyl group comprising up to one hydrogen atom for each two fluorine atoms.

15. The compound of claim 10 wherein Rf is a perfluoroalkyl group.

16. The compound of claim 10 wherein Rs is an alkylene group of 1 to 6 carbons.

17. A chemical compound having the formula:

O=Sn[Rs(Rf)]$_2$ wherein Rs is an alkylene group of 1 to 6 carbons or a phenylene group and wherein Rf is a fluorohydrocarbon group, a perfluorocarbon group, a fluorinated ether group or a fluorinated amine group.

18. The compound of claim 17 wherein Rs is an alkylene group of 1 to 6 carbons.

19. A chemical compound having the formula:

X$^1$X$^2$Sn[Rs(Rf)]$_2$ wherein X$^1$ and X$^2$ are independently, the same or different, H, N$_3$, OR$^1$, OOR$^1$ SR$^1$, SeR$^1$, CN, NC, NR$^1$R$^2$, a heteroaryl group, an alkyl group of 2 to 20 carbons, an alkenyl group, an alkynyl group, —C(O)R$^3$, M((Rs')(Rf'))$_3$, OM((Rs')(Rf'))$_3$ or OOM((Rs')Rf'))$_3$, wherein M is Si, Ge, or Sn, and wherein R$^1$ and R$^2$ are each independently the same or different H, an alkyl group, —SO$_2$R$^3$ or —C(O)R$^3$, wherein R$^3$ is an alkyl group or an aryl group, wherein Rs and Rs' are each independently the same or different an alkylene group of 1 to 6 carbons or a phenylene group, wherein Rf is a fluorohydrocarbon group of at least 3 carbons, a perfluorocarbon group of at least 3 carbons, a fluorinated ether group or a fluorinated amine group, and wherein Rf' is a fluorohydrocarbon group, a perfluorocarbon group, a fluorinated ether group or a fluorinated amine group.

20. The compound of claim 19 wherein Rs is an alkylene group of 1 to 6 carbons.

* * * * *